(12) United States Patent
Chen

(10) Patent No.: US 7,159,596 B2
(45) Date of Patent: Jan. 9, 2007

(54) FLOSS DISPENSER WITH DYNAMIC TENSION CONTROL

(76) Inventor: Chia-Ching Chen, 8, Lane 406, Da-Li Rd., Da-Li City, Taichung county (TW)

( * ) Notice: Subject to any disclaimer, the term of this patent is extended or adjusted under 35 U.S.C. 154(b) by 425 days.

(21) Appl. No.: 10/601,240

(22) Filed: Jun. 20, 2003

(65) Prior Publication Data

US 2004/0255972 A1    Dec. 23, 2004

(51) Int. Cl.
 *A61C 15/00* (2006.01)
(52) U.S. Cl. ...................................... 132/326
(58) Field of Classification Search ........ 132/322–326; 242/388.5, 395, 396.4, 410, 412, 412.1, 416, 242/417, 417.2, 577.1, 610.6, 586, 586.2, 242/587–587.2, 571.4, 571.7, 571.8, 579, 242/584.1
See application file for complete search history.

(56) References Cited

U.S. PATENT DOCUMENTS 3,871,393 A * 3/1975 Wharton .................... 132/326
4,495,957 A * 1/1985 Beggs et al. ................ 132/325
5,495,863 A * 3/1996 Bergman .................... 132/326
5,881,744 A * 3/1999 Lo ............................. 132/325
6,089,241 A * 7/2000 Lo ............................. 132/326
6,363,949 B1* 4/2002 Brown ....................... 132/325
6,497,237 B1* 12/2002 Ali ............................. 132/324
6,874,509 B1* 4/2005 Bergman .................... 132/325

* cited by examiner

*Primary Examiner*—Cris L. Rodriguez
*Assistant Examiner*—Rachel A. Running
(74) *Attorney, Agent, or Firm*—Leong C. Lei

(57) ABSTRACT

Provided is a floss dispenser comprises a housing defining at least a receiving chamber with a floss bobbin rotationally received therein. A floss fork is arranged at an end of the housing for bracing a section of floss thereon. A first tension-controlling device is arranged on the housing controlling a tension of the floss after the floss fork. And a tensioner is arranged adjacent to the feeding device controlling the tension between the floss bobbin and the floss fork.

Figure 1:
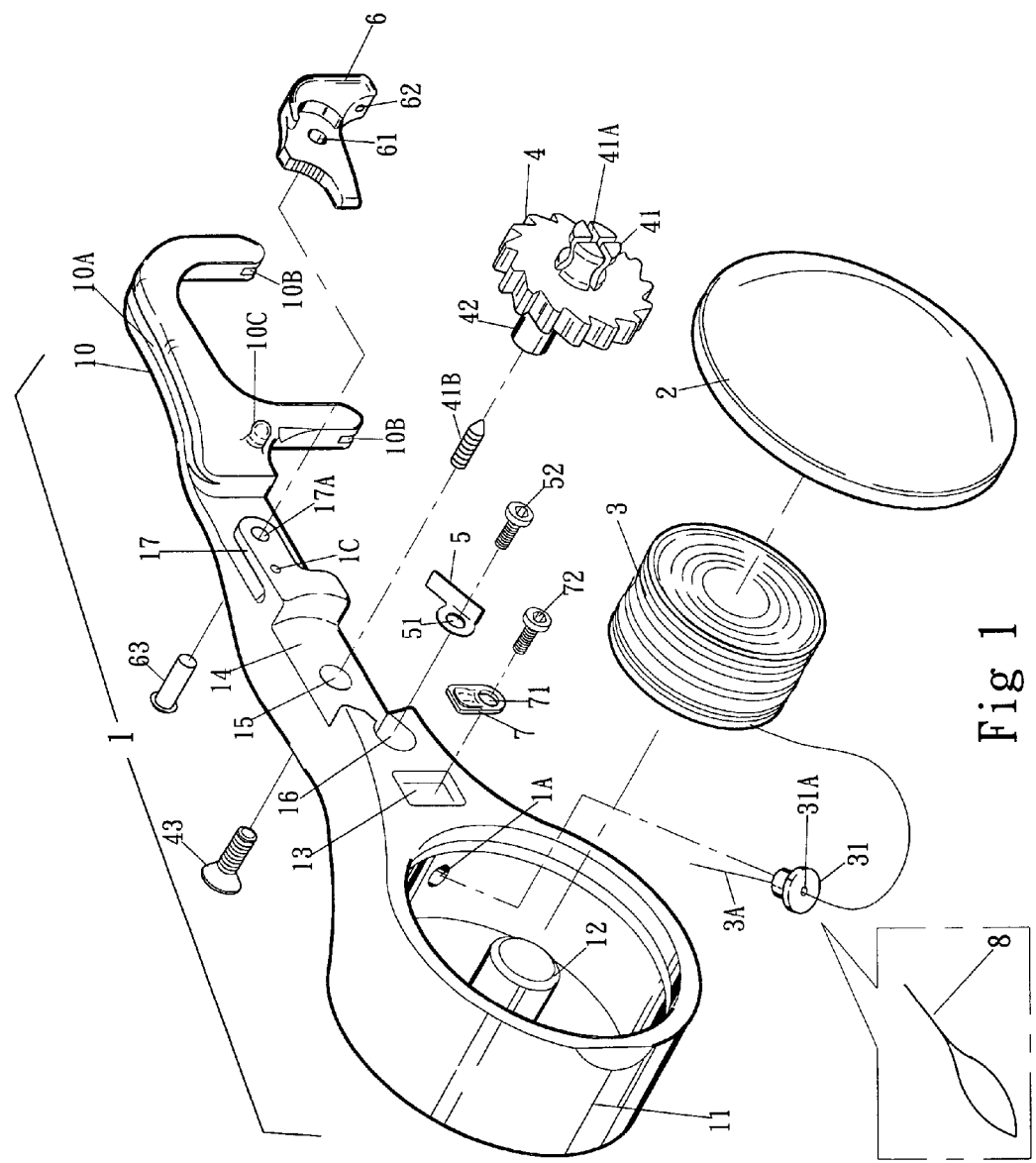
Figure 2:
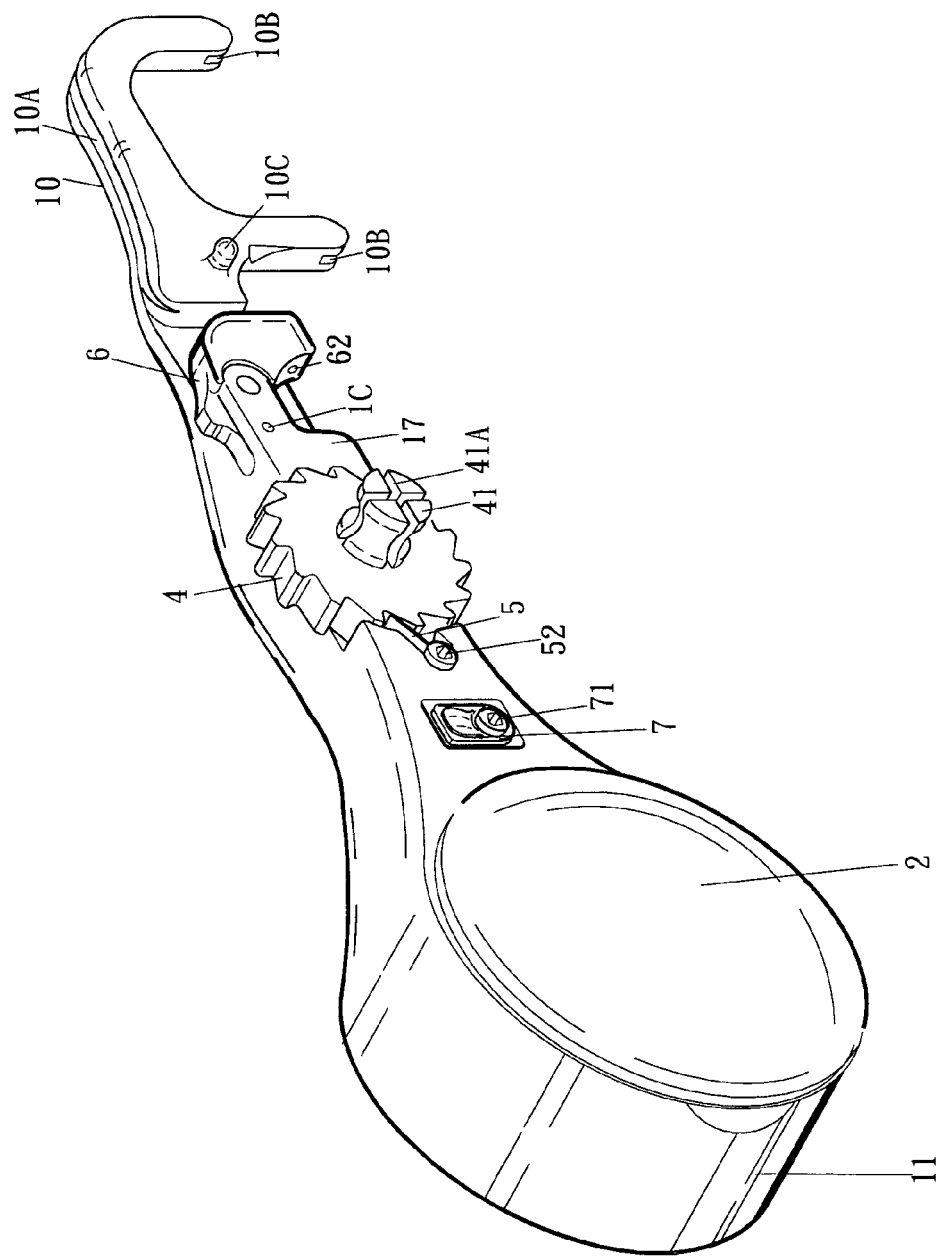

By the provision of the tensioner, the tension of the floss can be properly controlled during the flossing process, and the tension of the floss can be released after the flossing process.

10 Claims, 9 Drawing Sheets

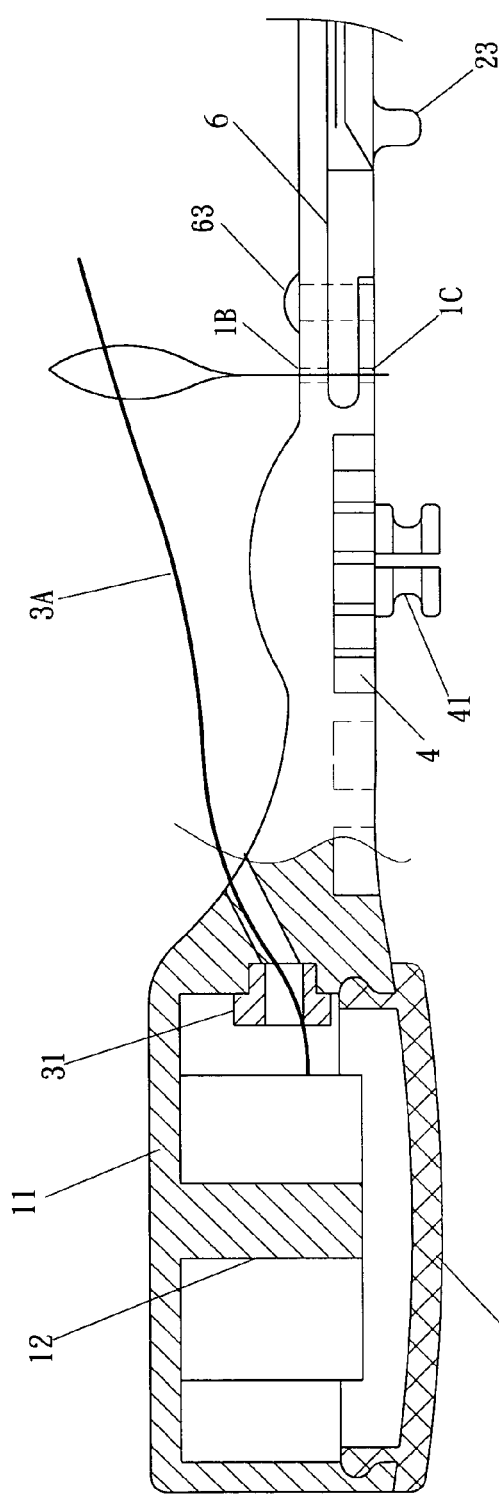
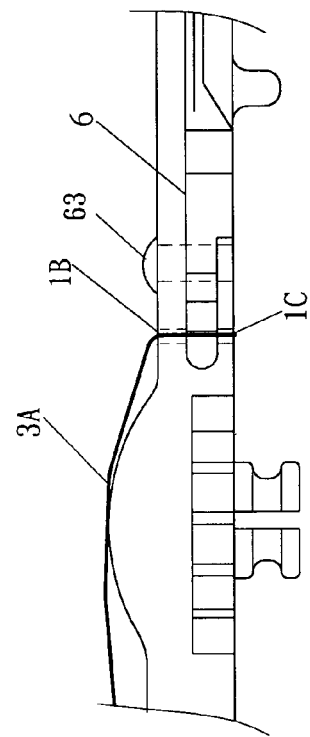
Fig 4
Fig 4A

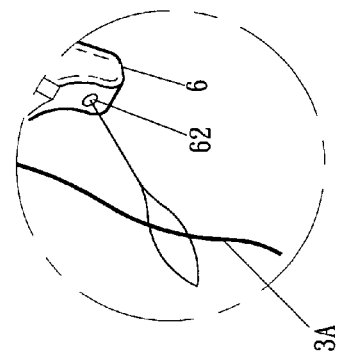
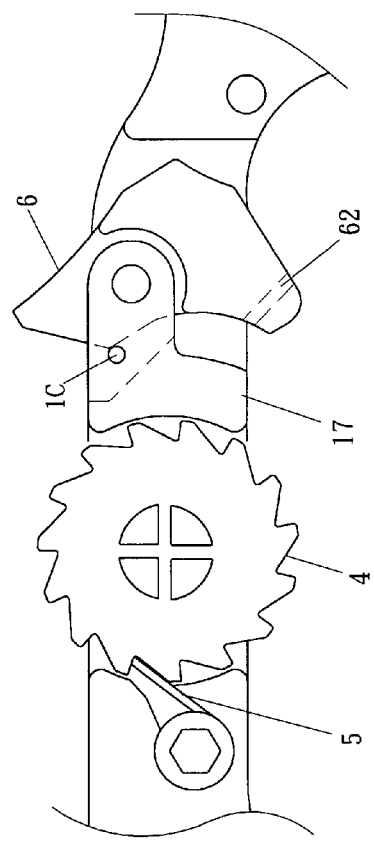
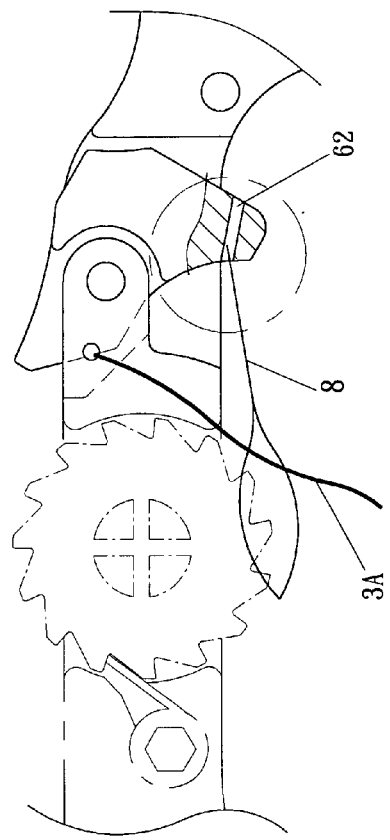

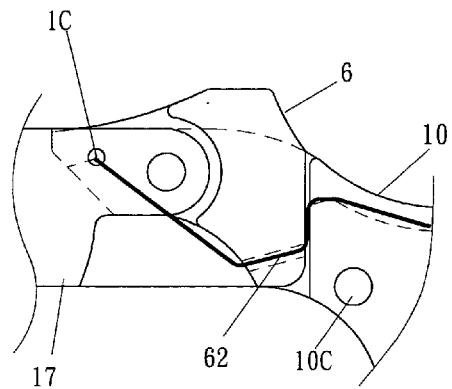
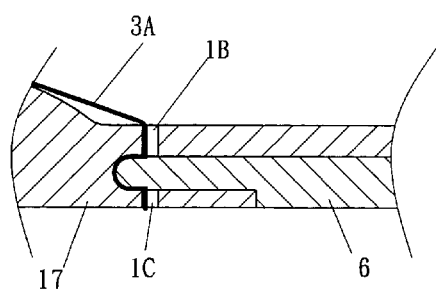
Fig 8
Fig 8A
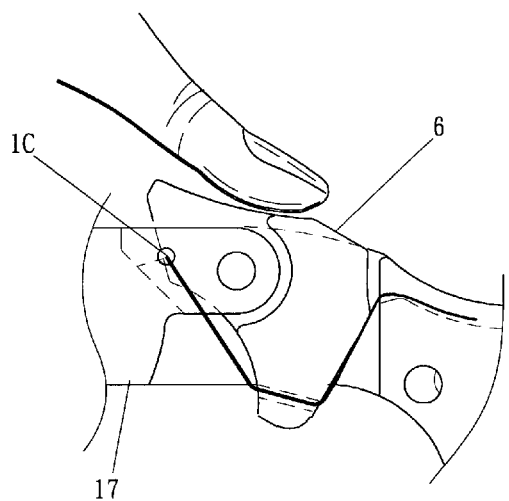
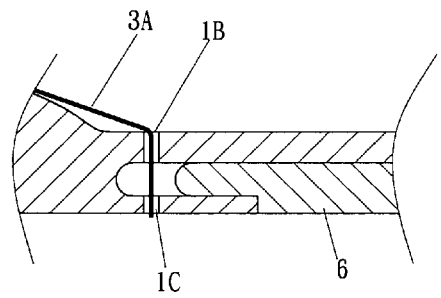
Fig 9
Fig 9A

FLOSS DISPENSER WITH DYNAMIC TENSION CONTROL

FIELD OF THE INVENTION

The present invention relates to a dental floss dispenser, and more particular to a floss dispenser integrating advantages of conventional toothpick as well as floss box. The floss dispenser includes a bracket on which the floss is robustly supported for facilitating easy and smooth cleaning process between the teeth. In addition, the floss can be replaced anytime according to the necessity. The floss dispenser features simple configuration while the length of floss for flossing can be economically used.

DESCRIPTION OF THE PRIOR ART

Conventionally, dental floss is used to remove food debris and dental plaque between teeth by flossing plaque out of the space between two teeth, extending the floss to gingival sulcus, and then sweeping along teeth surface thereby preventing any bacteria growing there. There are many commercial available floss in the form of floss box and toothpick for the dental cleaning purpose.

In use, a certain length of floss is cut from the floss box, and tensioned between fingers from both hands. Then the floss cuts into the space between two adjacent teeth, and with the upward and downward movement of the floss therealong, the food debris can be kicking off therefrom.

However, this conventional application has the following disadvantages. Firstly, hands carry bacteria and bring into the mouth during the cleaning process. Secondly, the length of the floss is hard to control. If it is too short, then it imposes a difficulty in cleaning, if it is too long, then it is surely a waste. Even there are toothpicks bonded with floss holder, this disposable toothpick is really not healthy to our environment from a pollution viewpoint.

SUMMARY OF THE INVENTION

It is an object of this invention to provide a floss dispenser in which the length of the floss can be accurately controlled, while the tension of the floss is also property controlled so as to provide a user-friendly application.

In order to achieve the object set forth, provided is a floss dispenser in accordance with the present invention comprises a housing defining at least a receiving chamber with a floss bobbin rotationally received therein. A floss fork is arranged at an end of the housing for bracing a section of floss thereon. A first tension-controlling device is arranged on the housing controlling a tension of the floss after the floss fork. And a tensioner is arranged adjacent to the feeding device controlling the tension between the floss bobbin and the floss fork.

By the provision of the tensioner, the tension of the floss can be properly and dynamically controlled during the flossing process, and the tension of the floss can be released after the flossing process.

BRIEF DESCRIPTION OF THE DRAWINGS

FIG. 1 is an exploded perspective view of a floss dispenser in accordance with the present invention;

FIG. 2 is an assembled view of FIG. 1;

FIG. 3 is an illustration showing a floss extending through an eyelet of a circular slot;

FIG. 3A is an enlarged view circled in FIG. 3;

FIG. 4 is an illustration showing the floss route through a first section of floss dispenser;

FIG. 4A shows the floss completes its route on the first section;

FIG. 5 shows the floss routes through a tension controller;

FIG. 5A shows details thereof;

FIG. 5B is an enlarged view thereof;

FIG. 6 shows the floss routes through a thread hole of a tensioner;

FIG. 7 is an illustration showing the floss is well supported on a bracket of the floss dispenser;

FIG. 7A is a top view thereof;

FIG. 8 is an illustration showing the movement of the tensioner of the floss dispenser;

FIG. 8A shows the floss is locked by the tensioner;

FIG. 9 shows the floss is released by the tensioner for replacing new floss;

FIG. 9A shows a top view of FIG. 9 and

FIG. 10 shows used floss is cut off by a cutter.

DETAILED DESCRIPTION OF PREFERRED EMBODIMENT

Referring to FIG. 1, an exploded view of a floss dispenser according to the present invention is shown. The floss dispenser generally includes a housing 1 on which a detachable cover 2 is attached. The floss dispenser further includes a floss bobbin 3, a ratchet 4 and stopper 5, a tensioner 6 and a cutter 7.

The housing 1 defines a receiving chamber 11 in which a bobbin shaft 12 is mounted. The receiving chamber 11 further defines a feeding hole 1A and a side feeding hole 1B (see FIGS. 4 and 4A). The housing 1 further includes a cutter cell 13 adjacent to the receiving chamber 11 in a middle portion thereof. A cutting knife 7 is assembled into the cutter cell 13 by means of a screw 72 through a hole 71 of the cutting knife 7. The housing 1 further includes a ratchet socket 14 in which the ratchet 4 is installed. The ratchet 4 is moveably assembled in the ratchet socket 14 by a screw 43 and other assembling kits which will be described in detail later. Adjacent to the ratchet socket 14, a stopper cell 16 in communication with the ratchet socket 14 is provided. The stopper 5 is mounted in the stopper cell 16 by means of a screw 52 through a mount 51 thereof. The stopper 5 extends into teeth of the ratchet 4 such that the ratchet 4 can rotate along clockwise.

Adjacent to the ratchet socket 14, a tensioner bracket 17 is provided. The tensioner bracket 17 defines a feeding hole 1C and a shaft hole 17A for assembling the tensioner 6 therein. The tensioner 6 is mounted into the tensioner bracket 17 by means of a rivet 63. Finally, at the opposite end of the receiving chamber 11, a floss fork 10 is provided. The floss fork 10 defines a guiding slot 10A along its outer surface, and a pair of notches 10B at ends of the fork for supporting the floss therebetween. A post 10C is provided adjacent to an inner beam of the fork 10.

Referring to FIG. 2, after the floss bobbin 3 is disposed within the receiving chamber 11, the cover 2 is attached so as to enclose the bobbin 3 therein. A detachable threader 31 is selectively provided for inserting into the feeding hole 1A. The threader 31 includes a passage 31A through which the floss extends.

As mentioned above, the ratchet 4 is assembled into the ratchet socket 14 by means of the assembling kit which is configured by a slotted shaft 41 and a shaft 42. A rubber member 41B is selectively arranged within slots of the slotted shaft 41. By this arrangement the ratchet 4 can be assembled into a supporting hole 15 of the ratchet socket 14 by means of the screw 43.

Figure 3:
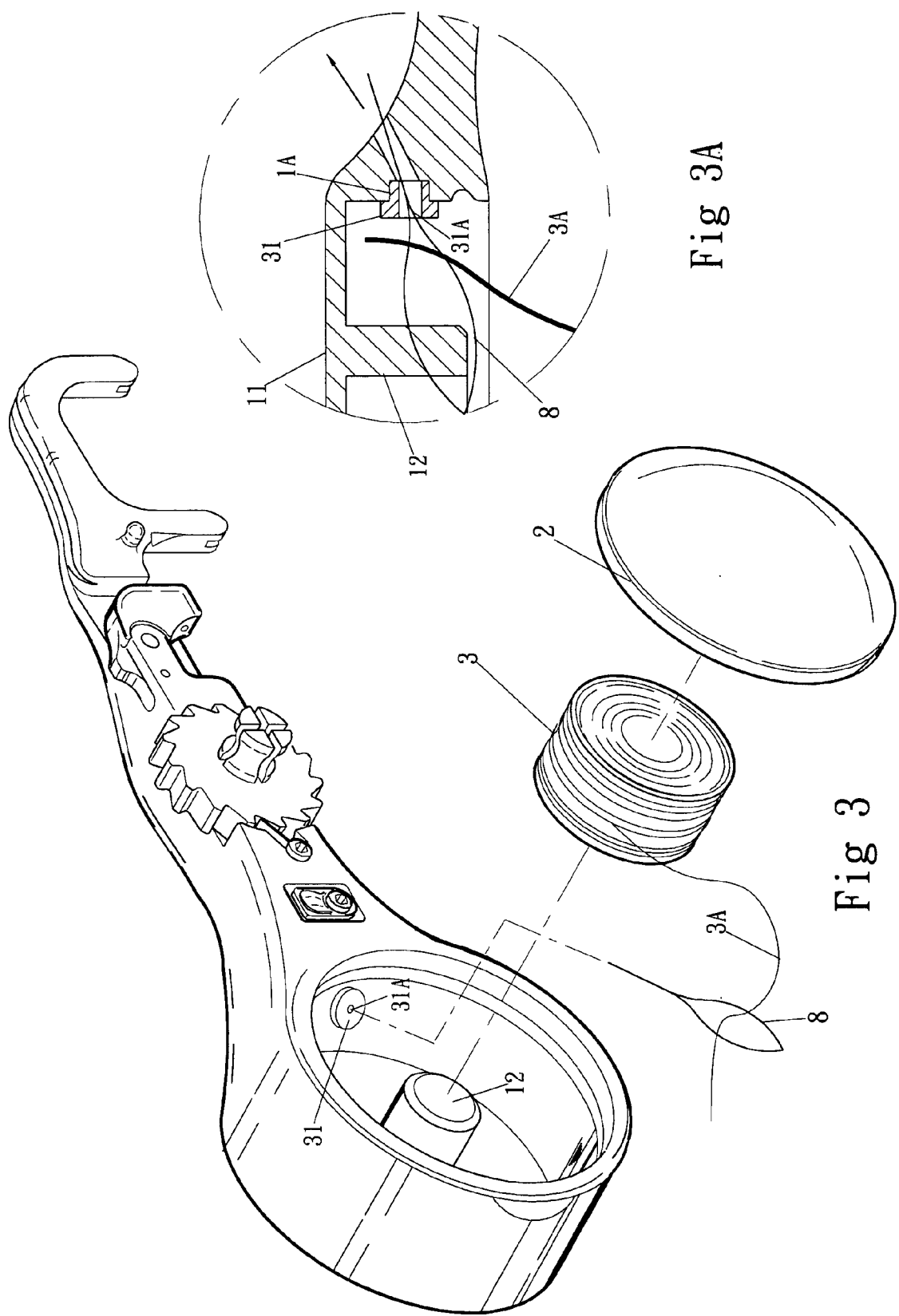
Figure 6:
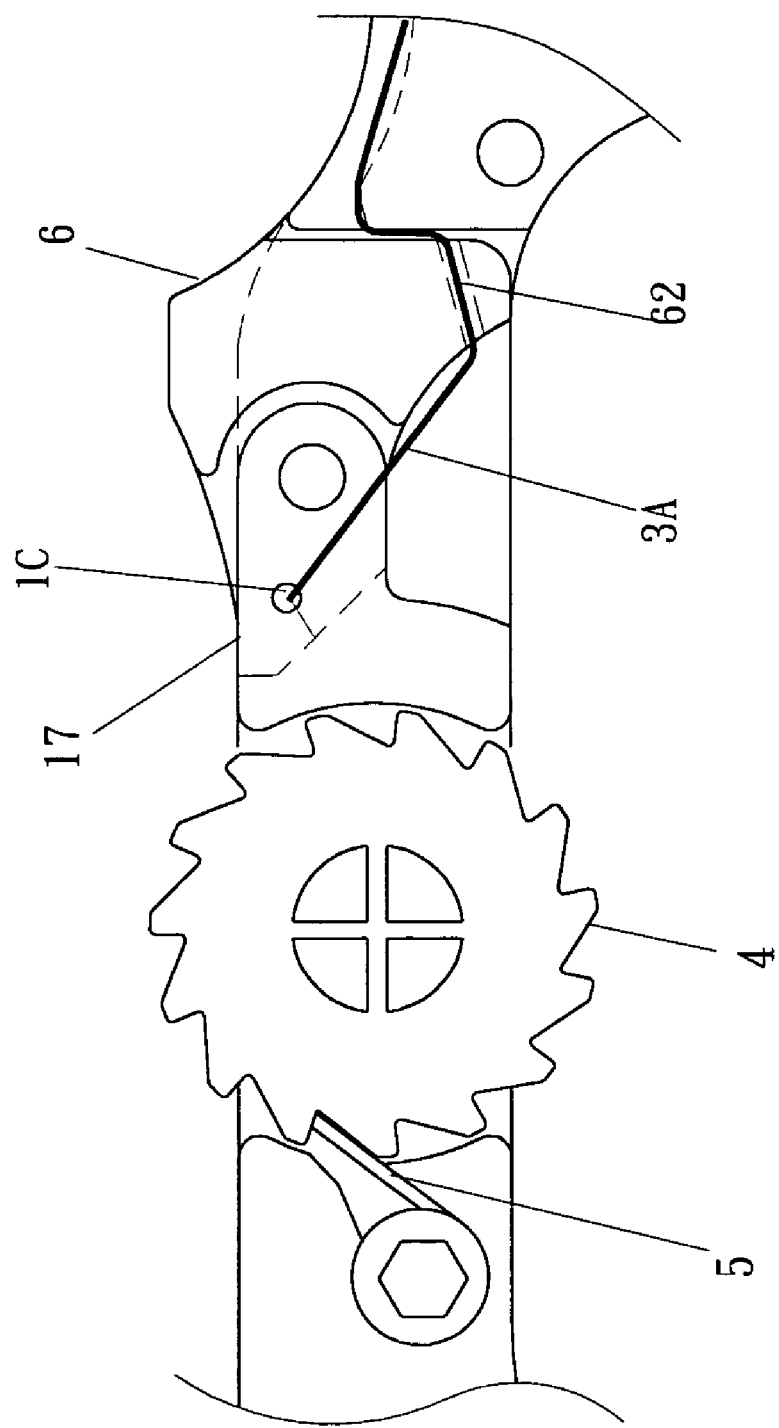

Referring now to FIGS. 3, 4 and 5, a floss route along the dispenser is shown in detail. After the floss bobbin 3 is rotationally assembled into the receiving chamber 11, the floss is firstly extended through the passage 31A of the threader 31. Then the floss passes further through the side feeding hole 1B, the feeding hole 1C of the tensioner bracket 17 and is thereafter further extended through a passage 62 of the tensioner 6.

Firstly, a threading device 8 is used to move the floss 3A through the passage 31A of the threader 31. Then the floss 3A is routed through the feeding hole 1A and comes out therefrom to one side of the housing 1. The floss 3A is further threaded through the side feeding hole 1B and the feeding hole 1C of the tensioner bracket 17, as shown in FIGS. 4A and 4. Then the tensioner 6 is slightly moved such that the floss 3A can pass through the passage 62 of the tensioner 6. By this arrangement, the tensioner 6 applies a certain tension to the floss 3A.

Figure 7A:
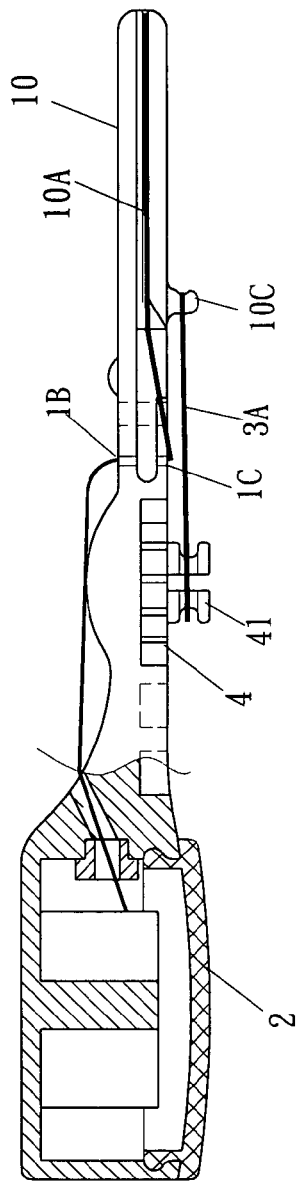
Figure 7:
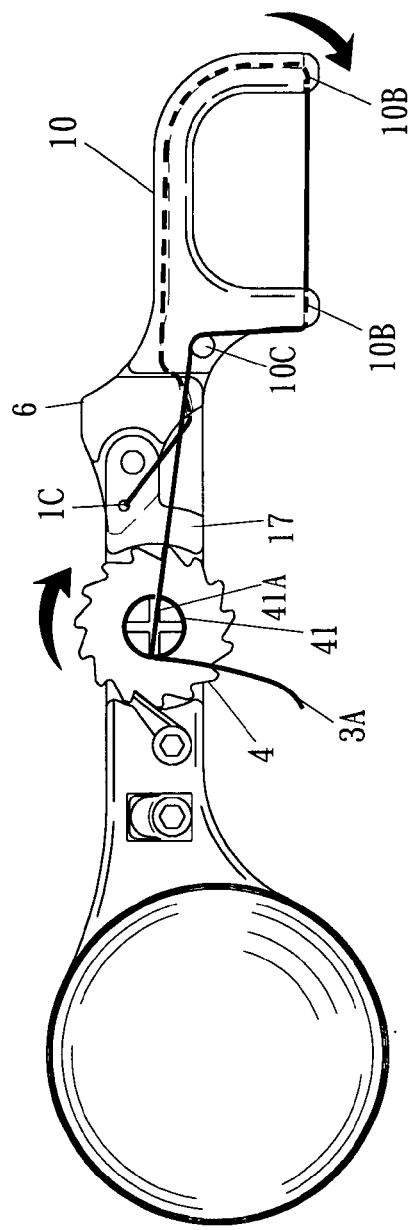

Then, the floss 3A routes through the guiding slot 10A of the floss fork 10, as shown in FIGS. 7 and 7A. The floss 3A then routes along the notches 10B of the fork, and is finally anchored at the post 10C. The floss 3A further routes to the slotted shaft 41 of the ratchet 4 and extends through the slots 41A of the slotted shaft 41 to be held thereby. Preferably, the slotted shaft 41 is inserted with a rubber 41B, which imposes a friction to the floss 3A, the floss 3A can then be securely held. As a result, the floss 3A completes its routing and holds with proper tension.

When the floss 3A completes its routes and a user would like to use it to floss, the user may slightly press on the tensioner 6 such that the floss 3A is tensioned. Then the user may rotate the ratchet 4 so as to further tension the floss 3A by the arrangement between the ratchet 4 and the stopper 5. Finally, the user can use the floss 3A spanning between the floss fork 10 for flossing. Specially, the tension of the floss 3C can be adjusted anytime by the ratchet 4.

Figure 10:
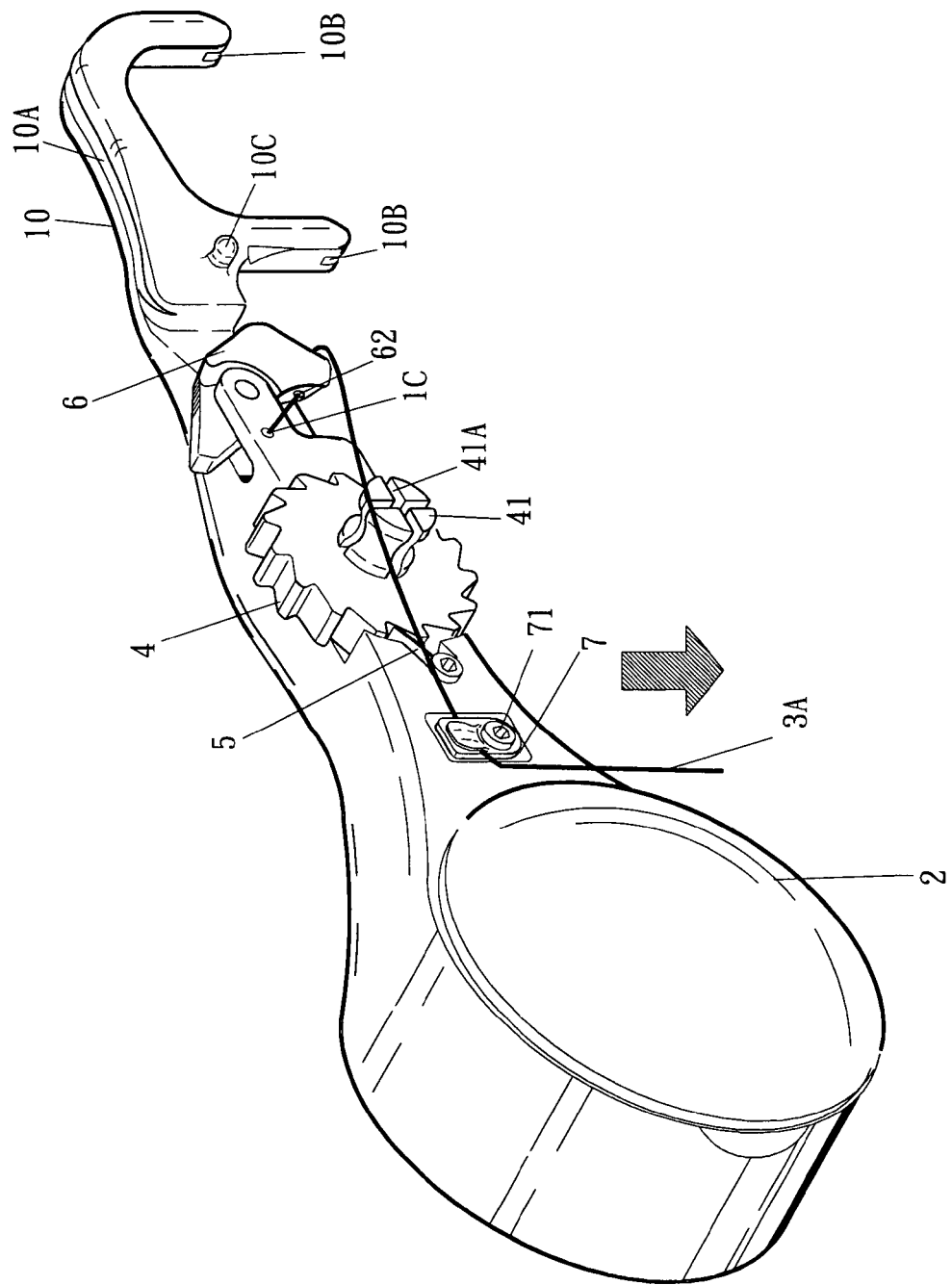

After a section of floss 3A is used, the used floss 3A can be easily replaced, as shown in FIGS. 9 and 9A. The floss 3A braced between the fork 10 can be easily released from the notches 10B by a further push back of the tensioner 6 so as to release the tension applied to the floss 3A. As a result, the floss 3A can be easily released from the notches 10B. Then the used floss 3A can be cut off by the knife 7, as shown in FIG. 10. A new section of floss 3A can be re-routed to the fork 10 according to the procedures described above. After the floss bobbin 3 is exhausted, a new floss bobbin 3 can be refilled and the user may start a cycle of flossing.

The floss dispenser made according to the present invention can be featured with at least the following advantages.

1. The floss dispenser made in accordance with the present invention features the advantages from both the floss box and the toothpick with floss holder. The user can easily use it to floss. In addition, the floss can be easily replaced while the floss can be economically controlled.

2. The floss dispenser made in accordance with the present invention further features a simplified configuration readily for handling. By the provision of the ratchet and tensioner, the tension of the floss can be accurately controlled thereby preventing the break of the floss during the flossing.

From the above description, it can be easily appreciated that the tension of the floss is controlled by both the ratchet after the floss routes through the post, and by the tensioner right before the floss reach the floss fork. This two stage controlling of the floss, especially the tensioner, provides a dynamic control of the tension of the floss. As such, the user may easily perform the flossing process.

It should be note that the specification relating to the above embodiment should be construed as exemplary rather than as limitation of the present invention, with many variations and modifications being readily attainable by a person of skill in the art without departing from the spirit or scope thereof as defined by the appended claims and their legal equivalents.

I claim:

1. A floss dispenser, comprising:
   a housing defining at least a receiving chamber with a floss bobbin rotationally received therein;
   a floss fork arranged at an end of the housing for bracing a section of floss thereon;
   a first tension controlling device arranged on the housing for controlling tension of the floss from the floss bobbin, and comprising a ratchet having a slotted shaft through which a portion of the floss extends for securely anchoring the floss; and
   a tensioner movably mounted to the housing and defining a passage through which the floss extends to selectively apply tension to the floss by the movement of the tensioner.

2. The floss dispenser as recited in claim 1, further comprising a cover removably attached to the housing to enclose the receiving chamber.

3. The floss dispenser as recited in claim 2, wherein the receiving chamber includes a feeding hole in which a threader having a passage is mounted.

4. The floss dispenser as recited in claim 1, wherein the ratchet is provided with a stopper such that the ratchet runs only in a single direction.

5. The floss dispenser as recited in claim 1, wherein the tensioner is mounted to the housing by a tensioner bracket of the housing.

6. The floss dispenser as recited in claim 1, wherein the housing provides a cutter so as to cut the floss to a suitable length.

7. The floss dispenser as recited in claim 1, wherein the floss fork includes a post for anchoring of the floss.

8. The floss dispenser as recited in claim 1, wherein the tensioner is movable in a direction to release the tension of the floss so as to allow the floss to be removed from the floss fork thereby releasing the floss therefrom.

9. The floss dispenser as recited in claim 1, further comprising a threader for easily threading the floss through feeding holes and passages of the housing.

10. The floss dispenser as recited in claim 1, wherein the floss routes from the receiving chamber, further through a passage of the tensioner, a guiding slot of the floss fork, then braced by notches defined in ends of the fork, anchoring around a post adjacent to the floss fork, and finally securely anchored to the feeding device.

* * * * *